US008634623B2

(12) United States Patent
Schmitt et al.

(10) Patent No.: US 8,634,623 B2
(45) Date of Patent: Jan. 21, 2014

(54) CORRECTION OF ARTIFACTS IN TIME-OF-FLIGHT MR ANGIOGRAPHY

(75) Inventors: Peter Schmitt, Weisendorf (DE); Michael Zenge, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 1050 days.

(21) Appl. No.: 12/624,478

(22) Filed: Nov. 24, 2009

(65) Prior Publication Data

US 2010/0128952 A1   May 27, 2010

(30) Foreign Application Priority Data

Nov. 24, 2008   (DE) .......................... 10 2008 058 740

(51) Int. Cl.
*A61B 6/03*   (2006.01)

(52) U.S. Cl.
CPC ........................................ *A61B 6/03* (2013.01)
USPC .......................................................... 382/131

(58) Field of Classification Search
USPC .............................. 324/309; 382/131; 600/410
See application file for complete search history.

(56) References Cited

U.S. PATENT DOCUMENTS

| | | | |
|---|---|---|---|
| 6,795,723 B1 | 9/2004 | Liu | |
| 8,121,382 B2* | 2/2012 | Bohm et al. | 382/132 |
| 2002/0009216 A1* | 1/2002 | Ogino | 382/131 |
| 2002/0094114 A1* | 7/2002 | Ogino | 382/128 |
| 2009/0143666 A1* | 6/2009 | Edelman et al. | 600/410 |

OTHER PUBLICATIONS

Kholmovski et al., Correction of Slab Boundary Artifact using Histogram Matching, 2002, Journal of Magnetic Resonance Imaging, vol. 15, pp. 610-617.*

Atkinson et al., Improved MR Angiography: Magnetization Transfer Suppression with Variable Flip Angle Excitation and Increased Resolution, 1994, Radiology, vol. 190, pp. 890-894.*
Lui et al., Sliding Interleaved kY (SLINKY) Acquisition: A Novel 3D MRA Technique with Suppressed Slab Boundary Artifact, 1998, Journal of Magnetic Resonance Imaging, vol. 8, pp. 903-911.*
"A Three-dimensional MRI Atlas of the Mouse Brain with Estimates of the Average and Variability," Kovacevic et al, Cerebral Cortex, vol. 15 (2005) pp. 639-645.
"A Nonparametric Method for Automatic Correction of Intensity Nonuniformity in MRI Data," Sled et al, IEEE Trans. on Medical Imaging, vol. 17, No. 1 (1998) pp. 87-97.
"A Non-parametric Method for Automatic Correction of Intensity Non-uniformity in MRI Data," Sled Master Thesis, McGill University (1997).
"Correction of Slab Boundary Artifact using Histogram Matching," Kholmovski et al, Proc. Int. Soc. Mag. Reson. Med. (2001) p. 738.
"Sequential Three-Dimensional Time-of-Flight MR Angiography of the Carotid Arteries," Ding et al, AJR, vol. 163 (1994) pp. 683-688.
"Cervical Carotid MR Angiography with Multiple Overlapping Thin-Slab Acquisition," Blatter et al, AJR, vol. 161 (1990) pp. 1269-1277.

* cited by examiner

*Primary Examiner* — Toan Ton
*Assistant Examiner* — John Corbett
(74) *Attorney, Agent, or Firm* — Schiff Hardin LLP

(57) ABSTRACT

In a method and magnetic resonance (MR) apparatus for correction of artifacts in time-of-flight (TOF) MR angiography, MR signals are acquired in a target volume with the TOF MR angiography technique to generate multiple MR angiography images, pixels with background signal are identified in the angiography images by separation of these pixels from noise and vessel pixels, a signal profile of the pixels with background signal is determined across the target volume, and the MR signal of a predetermined set of pixels of the target volume is normalized with the signal profile of the pixels with background signal.

11 Claims, 3 Drawing Sheets

CORRECTION OF ARTIFACTS IN TIME-OF-FLIGHT MR ANGIOGRAPHY

BACKGROUND OF THE INVENTION

1. Field of the Invention

The invention concerns a method for correction of MR signals that have been acquired with a time-of-flight (TOF) MR angiography technique, as well as an MR system to implement the correction.

2. Description of the Prior Art

In time-of-flight MR angiography, images of the vessel structure of an examination subject are generated with the use of gradient echo sequences. This angiography method is based on the fact that spins that remain stationary in a slice are saturated by many RF pulses, and therefore deliver little signal, while spins that flow perpendicular to the excited slice are replaced with new spins that can deliver markedly more signal. A high contrast between vessels and the remaining stationary tissue that supplies the background signal can be generated based on this phenomenon.

In the case of the excitation of a three-dimensional target volume that contains more than one slice, multiple RF excitation pulses that depend on the flow speed and the slice thickness of the individual slices in the target volume act on the blood flowing in. In order to prevent the signal intensity in the vessels from decreasing due to a saturation of the spins flowing into the target volume, the flip angles are varied across the target volume in order to obtain a homogeneous vessel signal across said target volume. This variation of the flip angles in the excitation of the spins, however, leads to a gradient in the signal intensity curve in the pixels with background signal. In the present case, "pixels with background signal" means those pixels that do not show a vessel in the MR angiography image and do not show the noise outside of the examined tissue, but rather the non-flowing tissue surrounding the vessel. Usually, acquisitions with multiple overlapping target volumes are necessary to show a vessel structure. If multiple overlapping target volumes are now acquired, respective signal intensity gradients result in the pixels with background signal in the different target volumes. In the assembled MR angiography image of the individual target volumes, this now leads to edge artifacts between the individual target volumes, known as the venetian blind artifact.

In "Sliding Interleaved $k_y$ (SLINKY) Acquisition: A Novel 3D MRA Technique with Suppressed Slab Boundary Artifact" by Kecheng, Liu et al. in JMRI 1998; 8, Pages 905-911, a new acquisition strategy is proposed to reduce this artifact, but this technique has not yet become established in practice.

SUMMARY OF THE INVENTION

It is an object of the present invention to provide a method with which such venetian blind artifacts can be reliably reduced.

According to a first aspect of the invention, a method is provided in which the MR signals are acquired in a target volume with the TOF MR angiography technique to generate multiple MR angiography images in the target volume. Furthermore, the pixels with background signal are identified in the angiography images by these background pixels being separated from the noise pixels and vessel pixels. In a further step, a signal profile is determined in the pixels with background signal across the target volume. When the signal profile in the background pixels is known, the MR signal of a predetermined set of pixels of the target volume can be normalized with the signal profile of the background pixels, so the effect of the signal intensity gradient in the background pixels can be removed or reduced. In particular, the artifacts at the boundaries between the target volumes in a composite MR image can be reduced with the method described above when multiple target volumes with partially overlapping regions are acquired.

The predetermined set of pixels can correspond to the set of background pixels. Furthermore, it is possible that the set corresponds to all pixels of the target volume.

According to a preferred embodiment, the target volume is acquired in multiple slices, wherein the MR signal is normalized via the signal profile of the pixels with background signal in the individual slices. The signal profile across the target volume can be approximated via the determination of the background signals in the individual slices.

The pixels with background signal are advantageously determined by segmentation of the generated MR images. The segmentation can be implemented depending on the signal intensity in the individual pixels. The pixels with background signal can be quite reliably differentiated from other signals, for example pixels with vessel signals or noise signals. It is thus possible in a simple manner to separate the pixels with background signal from the remaining pixels in the MR image and to determine the signal profile with the removed background pixels. In particular, the use of the signal intensity is independent of the number of pixels with vessel information or the number of noise pixels, wherein the ratio of these individual pixels changes across the individual slices. Since the TOF MR angiography typically generates a relatively high contrast between vessels and background signals, the method for identification of the pixels with background signal is very robust and delivers the correct results. This post-processing of the detected MR signals does not affect the signal acquisition itself but rather is based on a post-processing of the generated signals or, respectively, images.

Naturally, other segmentation methods can also be applied with which the identification of the background signals is possible, for example via segmentation of the generated MR images via edge detection or the like.

In one embodiment of the invention, the signal intensity distribution in the different slices of the background volume is determined, wherein the pixels with background signal can be identified with the aid of the signal intensity distribution. Given the use of the signal intensity distribution, the pixels with high signal intensity (vessels) and the pixels with very low signal intensity (noise pixels) can then be identified and removed, whereby the pixels with background signal remain. Different static quantities (for example the variance of the signal distribution) can be used in the determination of the background pixels from the signal intensity distribution.

In the event that multiple overlapping target volumes with respective multiple slices are acquired, averaged signal intensities of pixels with background signal can be calculated from predetermined slices of each target volume. These averaged signal intensities of the predetermined slices can be used for normalization of all slices in the various target volumes. For example, it is therefore possible to use a predetermined slice at a predetermined position within the target volume, to approximate a signal profile with the signal intensities of the background signal in these predetermined slices, and to use the approximated profile in order to normalize the background signal of each slice in the different target volumes.

Furthermore, morphological information can also be taken into account, for example the typical cylindrical structure of the bright vessel signals or the presence of fat under the skin, which likewise supplies a bright signal. Bright structures in the image at the edges of an examination subject can therefore be identified as fat and not as vessel. This can in particular be helpful in the separation of signals of vessel pixels and fat pixels. As an alternative to the use of the signal profile from the acquired MR images, the signal profile can also be calculated under consideration of the variation of the flip angle across the target volume, wherein additional signal characteristics of the examined tissue (for example the relaxation times, proton densities or MTC (magnetization transfer contrast)) are taken into account in order to calculate an approximated slice profile across the target volume.

The invention furthermore concerns an MR system with a pulse sequence control unit to acquire the MR signals in the target volume with the time-of-flight MR angiography technique; a unit to identify the background signal pixels; and a computer which determines the signal profile of the background pixels across the target volume and which normalizes the MR signal of the target volume or, respectively, the background pixels with the signal profile of said background pixels.

The MR system, in particular the computer, operates as was described above in detail.

DESCRIPTION OF THE PREFERRED EMBODIMENTS

Figure 1:
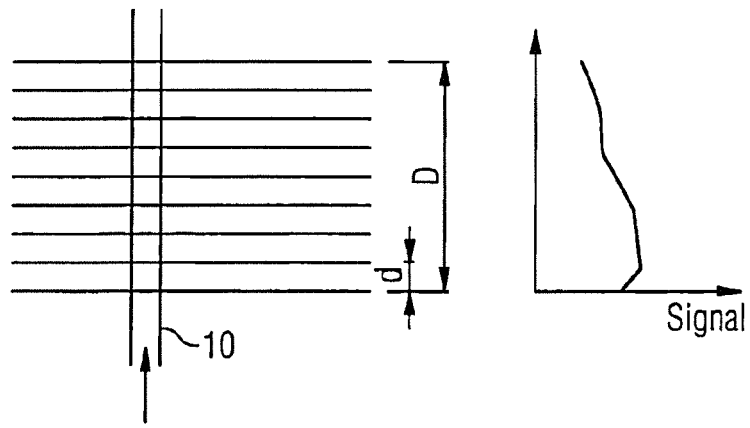
FIG. 1 shows an intensity profile for spins flowing into a target volume.
Figure 5:
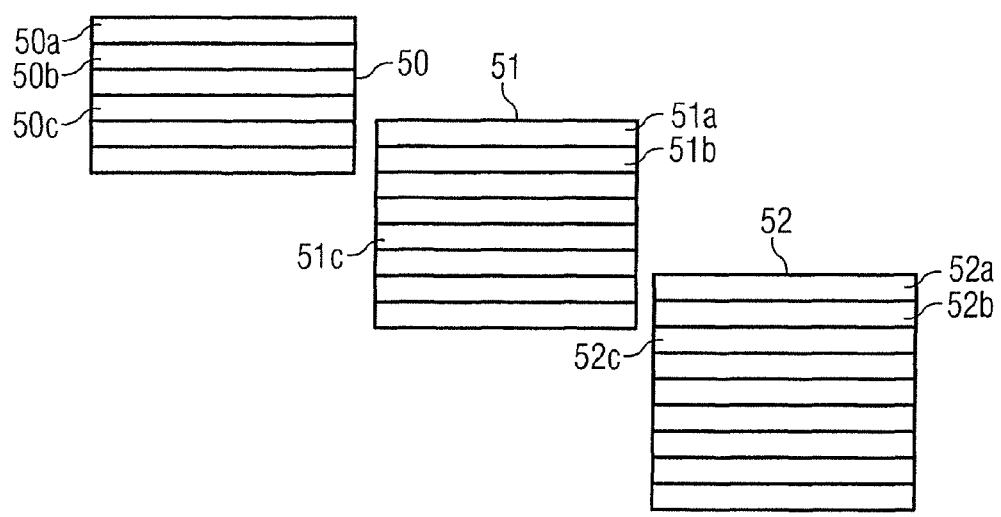
FIG. 5 schematically shows multiple target volumes that are respectively acquired in individual slices in order to subsequently be assembled into a complete angiography image.

In FIG. 1 it is shown how, given flow through a vessel 10 in a target volume with the slice thickness D, the signal intensity decreases when an RF excitation pulse with constant flip angle across the slice is used. The spins flowing from outside the target volume into the target volume are unsaturated in the vessel 10 and generate a higher signal intensity upon the subsequent signal readout with gradient echoes than spins that have already been exposed to the RF pulses in the target volume and that flow further in the target volume. Since these spins were already exposed to RF pulses, the magnetization contributing to the signal is lower so that—as is recognizable in FIG. 1—the signal intensity decreases in the flow direction. The precise signal curve hereby depends on the total thickness of the target volume D, the slice thickness d of the individual slices, the flow speed, the flip angle and the repetition time TR (the latter is defined as a time interval of two successive RF pulses). This effect is partially compensated in that RF pulses are used with which the flip angle increases across the target volume in the flow direction in order to obtain the magnetization decrease across the target volume in the flow direction. However, a signal intensity gradient that— if multiple target volumes are joined together—leads to artifacts at the edges of the joined volumes in the tissue surrounding the vessel 10. In MR angiographies of an examination subject (for example of the head) different target volumes 50, 51 and 52 that have a certain overlap among one another and that are shown next to one another only for reasons of clarity are acquired as shown in FIG. 5. Each of these target volumes can, for example, possess a slice thickness of 2-3 cm, wherein each target volume is acquired with a time-of-flight MR angiography sequence that is based on a 3D gradient echo sequence. A slice thickness of less than 1 mm is hereby achieved in the slice direction so that the individual slices 50a, 50b, 51a, 51b, 52a and 52b have a slice thickness of <1 mm. Other thickness of the target volumes and the individual slices can naturally also be applied. If flip angles that increase in the slice direction in the individual target volumes 50-52 are now used in the gradient echoes, the background signals of the spins outside of the vessels increases. If the individual target volumes 50, 52 are then assembled into an MR angiography image, intensity jumps (discontinuities) that are known as venetian blind artifacts thus result at the transitions between the individual target volume edges.

Figure 2:
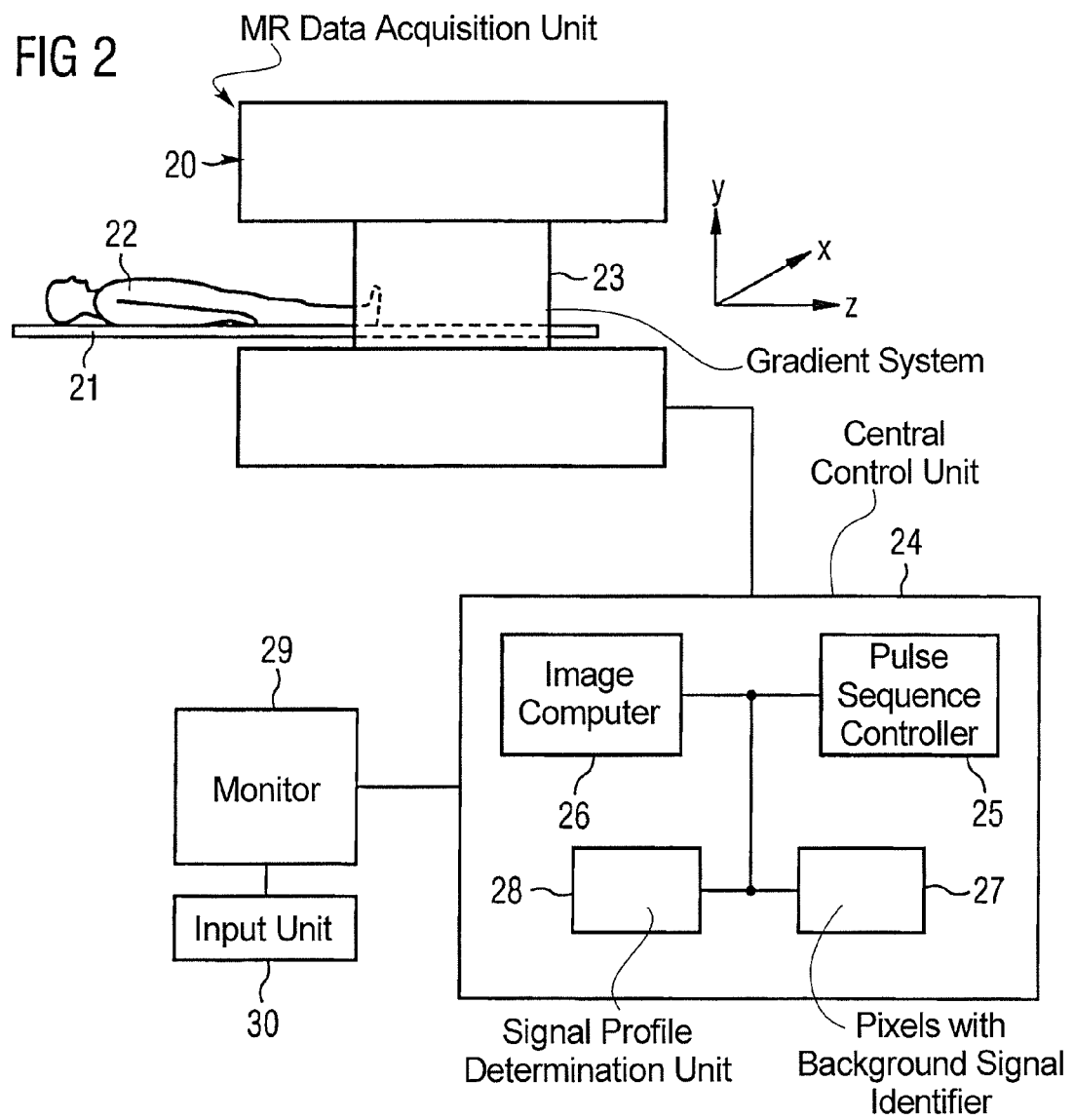
FIG. 2 schematically illustrates an MR system in accordance with the invention with which venetian blind artifacts in time-of-flight MR angiographies can be suppressed.

An MR system with which the artifacts described above can be suppressed at the edges is shown in FIG. 2. The MR system has a MR data acquisition unit (scanner) 20 that includes a magnet to generate a polarization field $B_0$. An examination subject 22 arranged on a bed 21 is moved into the center of the magnet in order to detect MR signals of the examination subject there. For spatial coding of the spins excited in the examination subject 22, a gradient system 23 is provided to generate linear magnetic field gradients. An RF system (not shown) radiates RF pulses into the examination subject, wherein MR signals can be acquired via a sequence of RF pulses and linear gradients and be converted into MR images. The precise mode of operation as to how MR images can be generated from the excitation of the spins in the examination subject is known to those skilled in the art and need not be explained in detail herein. The MR system furthermore has a central control unit 24. The central control unit 24 has a pulse sequence controller 25, an image computer 26 to calculate the MR images from the detected signals, an identifier 27 to identify pixels with background signal and a computer 28 that determines a signal profile of the pixels with background signal across an acquired target volume. The units 25-28 are each schematically represented as separate units. Naturally it is also possible that individual such units are connected into a single processing unit, for example the image computer 26 and the computer 28. Furthermore, a monitor 29 is provided to display the MR images and an input unit 30.

Figure 3:
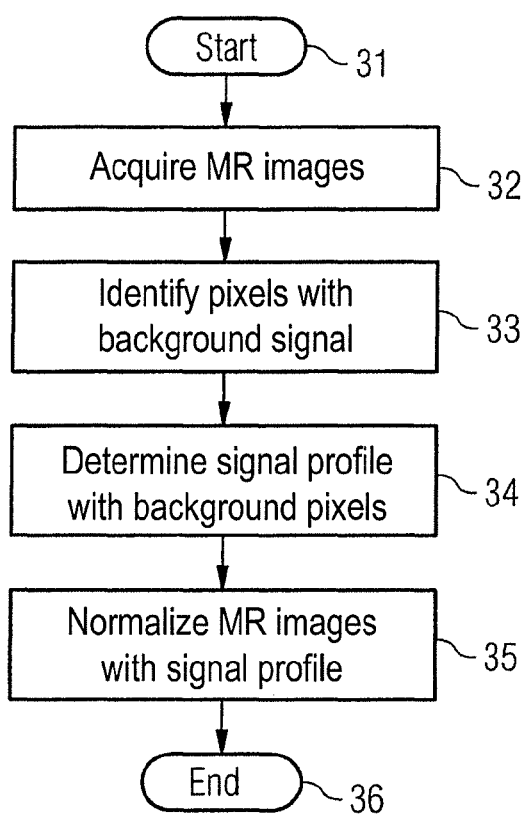
FIG. 3 is a flow chart of an embodiment of a method according to the invention to suppress the venetian blind artifacts.

The partial steps in a processing chain with which the venetian blind artifacts explained above can be suppressed or reduced are shown in FIG. 3. After the start of the method in Step 31, the MR angiography images are acquired in Step 32 as was explained in connection with FIG. 5. Pixels that represent flow perpendicular to the slice plane result in the MR image in the resulting MR angiography images that were acquired with the TOF MR angiography technique. Furthermore, pixels are present that result from the MR signal originating from tissue surrounding the vessels. These pixels have a much lower signal intensity in the MR angiography image than pixels with flow perpendicular to the image plane. Furthermore, pixels outside of the examined tissue are present that contain essentially only noise. The pixels that contain the background signal are identified by the unit 27 in Step 33. One possibility is to identify these background pixels by their signal intensity, since the differences in signal intensities between the three different types of pixels is relatively large so that the background pixels can be very reliably and simply separated from the vessel pixels and the noise pixels. When the pixels with background signal are known in the individual slices, an average signal intensity of the background pixels can be determined in every slice, for example. These averaged signal intensities of the background pixels in the individual slices yield, in totality, a slice profile across the target volume, which slice profile can be determined in Step 34. When the slice signal profile across the target volume of the background pixels is known, the signal intensity can as a whole be normalized in the individual slices such that the signal intensities in the MR image that contains all types of pixels is adapted such that the intensity profile of the background pixels is suppressed, so the background is more constant in the later-generated MR angiography image (Step 35). In another embodiment, only the background pixels are normalized, and not all pixels of the target volume. In the shown flow diagram, the method ends in Step 36 since here only the steps described in connection with the suppression of the venetian blind artifact are shown, and not all processing steps up to the concluding presentation of the MR angiography data set. The further steps comprise, among other things, a combination of the image information that is present "twice" in the overlap regions of two respective adjacent slices.

Figure 4:
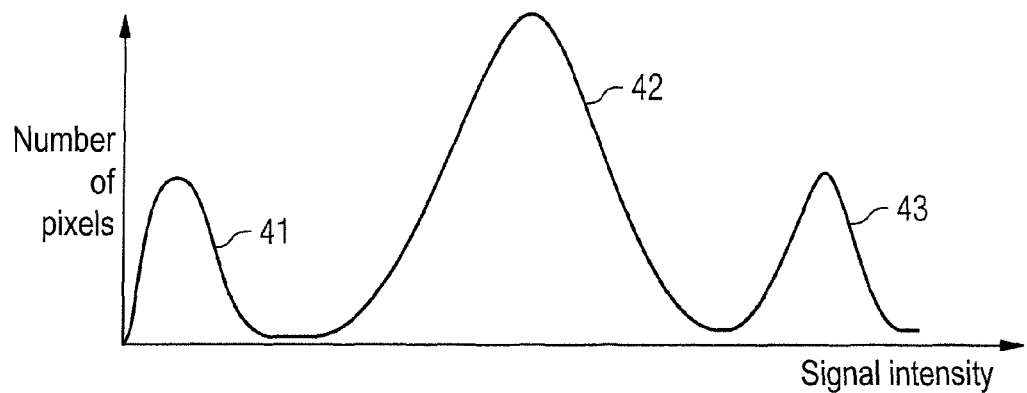
FIG. 4 schematically shows an intensity distribution of an MR angiography slice image.

The signal intensity distribution is schematically shown in a slice image in FIG. 4. The pixels with low signal intensity that do not show any tissue but rather only noise are shown under the curve 41 in the MR angiography image. Furthermore, the signal intensities with background signal in the MR angiography image are contained under the curve 43. These pixels have a higher signal intensity than the noise pixels but a much lower signal intensity than the pixels that are schematically shown under the curve 42, which correspond to the pixels for vessels having flow perpendicular to the image plane. The goal of step 34 in FIG. 3 is to identify the pixels that lie beneath the curve 42 or to discard the pixels that lie below the curves 41 and 43. Different statistical pars of the signal intensity distribution can be used for this, for example the variance of the curve 42.

If fat tissue is contained in the examined slice or in the MR signal, this is normally shown with a brightness similar to that of vessels. The fat would essentially appear in FIG. 4 as an additional peak that overlaps peak 43 or extends in the direction of peak 42. For the method it is important that only tissue that is shown darker (for example brain parenchyma or muscle tissue) is considered as background signal. Otherwise, the average background signal in the individual slices would turn out differently depending on its fat content, and the background signal gradient to be calculated would be correspondingly distorted.

For this reason the background signal must be separated not only from noise and vessel pixels but also from fat pixels in the event that these were not already suppressed in the signal acquisition.

As was explained at the beginning in connection with FIG. 5, multiple overlapping target volumes 50-52 are typically acquired in order to show a larger volume, for example the brain of the examination person. For example, the average of the background pixels can be determined in predetermined slices of each target volume (for example respectively the slices 50$c$, 51$c$ and 52$c$) to define the signal intensity profile in the individual target volumes. Slice profiles can then be approximated for the individual target volumes from the individual averages of the signal intensity of the background pixels, with which slice profiles the background signal of every individual slice is then normalized in the different target volumes. For example, instead of normalizing the individual slices 50$x$, 51$x$, 52$x$ ($x$=a, b, c, . . . ) using only their respective "own" average background signal, the assumption can also be used that the profiles within the volumes 50, 51, 52 should be identical. For this purpose, the average background signals of 50$x$, 51$x$, 52$x$ etc. can be averaged in turn, these can be normalized for all individual slices a through z, and all volumes can be normalized identically with this average profile. Alternatively, all background points from 50$x$, 51$x$, 52$x$ can be "tossed into a pot" and an average background signal of all slices with position x in the volume can be calculated from this, with which all of these slices can be normalized in turn.

In a further embodiment, with the knowledge of the variation of the flip angle across the target volume it is possible to calculate the signal intensity in the individual slices using additional signal characteristics (for example the examined tissue with the associated relaxation times and proton densities) instead of examining the detected signal intensity in the MR image. With this simulation of the signal intensities in the individual slices, a signal intensity profile of the background pixels can likewise be determined which can then in turn be used for normalization of the MR images.

Although modifications and changes may be suggested by those skilled in the art, it is the intention of the inventors to embody within the patent warranted hereon all changes and modifications as reasonably and properly come within the scope of his or her contribution to the art.

We claim as our invention:

1. A method for correcting magnetic resonance (MR) angiography images generated with a time-of-flight (TOF) MR angiography technique, said method comprising:

acquiring MR signals from a target volume in which blood flows in a vessel, by executing a TOF MR angiography sequence to generate multiple MR angiography data sets;

in a processor supplied with said MR angiography data sets, generating an MR angiography image respectively from each of said MR angiography data sets, thereby producing multiple MR angiography images each comprised of pixels, with said pixels comprising vessel pixels representing a vessel in which said blood flows, background pixels representing tissue in said target volume other than said vessels and said blood flowing therein, and noise pixels representing substantially only non-image-relevant noise;

in said processor, automatically identifying said background pixels in the respective MR angiography images by executing a separation algorithm that separates said background pixels from said noise pixels and said vessel pixels in each of said MR angiography images;

in said processor, determining a signal profile of said background pixels across an entirety of the target volume;

in said processor, normalizing the pixels in at least one predetermined set of pixels in the multiple MR angiography images of the target volume, with the signal profile of the background pixels with background signal, to produce normalized MR angiography images, as corrected MR images; and at an output of said processor, making said corrected MR images available in electronic form in at least one data file.

2. A method as claimed in claim 1 comprising acquiring said MR signals in data sets respectively from a plurality of slices in said target volume, generating one of said multiple MR angiography images for each slice respectively from one of said data sets, and normalizing pixels in the respective MR angiography images generated from the respective slices with the signal profile of background pixels in the respective MR angiography images.

3. A method as claimed in claim 2 comprising, in said MR angiography sequence, varying a flip angle across said target volume of RF excitation pulses radiated in said sequence, and determining the signal profile of said background pixels by calculating signal intensities in respective individual slices of said target volume dependent on said variation of said flip angle across said target volume and dependent on said signal characteristics of tissue contained in the target volume.

4. A method as claimed in claim 1 comprising identifying the background pixels by executing a segmentation algorithm dependent on a signal intensity of the individual pixels thereof, as said separation algorithm.

5. A method as claimed in claim 4 comprising acquiring said MR signals in data sets respectively from a plurality of slices in said target volume, generating one of said multiple MR angiography images for each slice respectively from one of said data sets, and normalizing pixels in the respective MR angiography images generated from the respective slices with the signal profile of background pixels in the respective MR angiography images, and determining a signal intensity distribution of said signal intensity of pixels in the respective MR angiography images, and identifying the background pixels from said signal intensity distribution.

6. A method as claimed in claim 1 comprising acquiring said MR signals from multiple overlapping target volumes, each having blood flowing in a vessel therein and each comprised of a plurality of slices, generating a respective MR angiography image from each slice of each of said target volumes, and, for each of said target volumes, averaging respective signal intensities of background pixels from predetermined slices therein and using the averaged signal intensities to normalize the MR angiography images in the respective different target volumes.

7. A method as claimed in claim 1 comprising identifying said background pixels using morphological information respectively represented by said background pixels in said vessel pixels when executing said separation algorithm.

8. A method as claimed in claim 1 comprising employing, as said predetermined set of pixels, a set of pixels selected from the group consisting of said pixels with background signal, and all pixels of said target volume.

9. A method as claimed in claim 1 comprising separating said background pixels from pixels representing fat in said target volume when executing said separation algorithm.

10. A method as claimed in claim 1 comprising:
operating said MR data acquisition unit in said TOF MR angiography sequence to acquire MR signals from a plurality of overlapping target volumes, in said respective multiple data sets;
in said processor, generating a respective MR angiography image for each of said overlapping target volumes;
in said processor, generating at least one composite MR angiography image from the respective MR angiography images of said overlapping target volumes;
in said processor, generating said signal profile of background pixels for said composite MR angiography image; and
normalizing said at least one composite MR angiography image with said signal profile of background images determined from said at least one composite MR angiography image.

11. A magnetic resonance apparatus for correcting magnetic resonance (MR) angiography images generated with a time-of-flight (TOF) MR angiography technique, comprising:
an MR data acquisition unit configured to execute a TOF MR angiography sequence to acquire multiple data sets of MR angiography signals from a target volume of a subject in the MR data acquisition unit;
a processor supplied with said multiple data sets, said processor being configured to generate MR angiography data sets, generating an MR angiography image respectively from each of said MR angiography data sets, thereby producing multiple MR angiography images each comprised of pixels, with said pixels comprising vessel pixels
representing a vessel in which said blood flows, background pixels representing tissue in said target volume other than said vessels and said blood flowing therein, and noise pixels representing substantially only non-image-relevant noise;
said processor being configured to identify said background pixels by executing a separation algorithm that separates said background pixels from said noise pixels and said vessel pixels in each of said MR angiography images;
said processor being configured to determine a signal profile of said background pixels across an entirety of the target volume;
said processor being configured to normalize the pixels in at least one predetermined set of pixels in the multiple MR angiography images of the target volume, with the signal profile of the background pixels, to produce normalized MR angiography images, as corrected MR images; and
said processor being configured to make said corrected MR images available in electronic form at an output of said processor, as at least one data file.

* * * * *